(12) United States Patent
Greaves et al.

(10) Patent No.: US 7,550,014 B2
(45) Date of Patent: Jun. 23, 2009

(54) COMPOSITION FOR DYEING KERATIN FIBERS AND A METHOD OF DYEING HAIR USING SAME

(75) Inventors: Erjena Greaves, New York, NY (US); Jeffrey T. Greaves, New York, NY (US)

(73) Assignee: Advanced Cosmetic Technologies, LLC, New York, NY (US)

( * ) Notice: Subject to any disclaimer, the term of this patent is extended or adjusted under 35 U.S.C. 154(b) by 175 days.

(21) Appl. No.: 11/381,061

(22) Filed: May 1, 2006

(65) Prior Publication Data

US 2007/0251024 A1 Nov. 1, 2007

(51) Int. Cl.
*A61Q 5/10* (2006.01)

(52) U.S. Cl. .................. 8/405; 8/425; 8/435; 8/552; 8/629; 8/637.1; 8/646

(58) Field of Classification Search .......... 8/405, 8/435, 552, 637.1, 629, 646, 425
See application file for complete search history.

(56) References Cited

U.S. PATENT DOCUMENTS

| | | | |
|---|---|---|---|
| 4,358,286 A | 11/1982 | Grollier | |
| 5,725,602 A | 3/1998 | Belcour-Castro | |
| 5,725,603 A * | 3/1998 | Audousset et al. | 8/405 |
| 5,865,853 A | 2/1999 | Schmitt | |
| 6,592,632 B2 | 7/2003 | Vainshelboim et al. | |
| 6,905,523 B2 | 6/2005 | Vainshelboim et al. | |
| 2001/0042276 A1 * | 11/2001 | Kawasoe et al. | 8/405 |
| 2003/0145395 A1 | 8/2003 | Murakami | |
| 2003/0159221 A1 | 8/2003 | Lang | |
| 2005/0071931 A1 | 4/2005 | Yoshida et al. | |
| 2005/0193501 A1 | 9/2005 | Chan et al. | |
| 2006/0246025 A1 | 11/2006 | Hayes et al. | |
| 2006/0265818 A1 | 11/2006 | Seiler et al. | |
| 2007/0199159 A1 | 8/2007 | Schmenger et al. | |

FOREIGN PATENT DOCUMENTS

EP  1426 028 A1 * 9/2004
JP  2001-162103 A  6/2001

OTHER PUBLICATIONS

English Abstract of the Japanese Patent No. 10182372 A.*
The Dyeing of Textile Fibers Theory and Practice by Joseph Rivlin, 1992, 98 Pages, Philadelphia College of Textiles and Science, Philadelphia, Pennsylvania 19144.
Dermatology/7 The Science of Hair Care Edited by Charles Zviak, L'Oreal, Paris, France, 27 Pages, (1986).
Colorants for Non-Textile Applications Edited by H.S. Freeman, 2000, 32 Pages, North Carolina State University, Raleigh, NC and A.T. Peters, University of Bradford BD7 1DP UK.
Shelton, Karen Marie, "Non-toxic Hair Color Facts," www.hairboutique.com, Aug. 18, 2001, 7 pages.

* cited by examiner

*Primary Examiner*—Eisa B Elhilo
(74) *Attorney, Agent, or Firm*—Wiggin and Dana LLP

(57) ABSTRACT

A composition for dyeing keratin fibers that contains 0.1 to 30 percent of at least one substantially pure plant dye material obtained using solvent or supercritical CO2 extraction combined with 0.01 to 5 percent of active metal in a metal or mineral salt capable of acting as a mordant as a two part hair color system. The addition of the encapsulation of one or both components allows the use of the plant dye in combination with the metal or mineral salt in a one part hair color system.

19 Claims, No Drawings

COMPOSITION FOR DYEING KERATIN FIBERS AND A METHOD OF DYEING HAIR USING SAME

FIELD OF THE INVENTION

This invention relates to hair dyes, specifically to the use of substantially pure plant dye substances obtained by solvent or supercritical CO2 extraction, with or without metallic or mineral salts, to make intense, fast-acting, long lasting hair dyes.

BACKGROUND OF THE INVENTION

Synthetic hair color formulations currently on the market typically fall into one of two categories: permanent and semi-permanent.

Permanent hair color formulations consist primarily of oxidative dye systems based on the dual action of two types of precursors—bases (primary intermediates) and modifiers (couplers). Bases are typically aromatic diamines, diaminophenoles, aminophenols, while couplers are typically m-diamines, m-aminophenols and polyphenols (Charles Zviak, The Science of Hair Care, Marcel Dekker Inc., New York, 1986, pp. 265-268; Joseph Rivlin, The Dyeing of Textile Fibers, PCT&S, Philadelphia, 1992, pp. 30-52). The wash fastness of permanent dyes is about 30-40 shampoo cycles. There are, however, a number of issues with permanent dyes. The primary amine used in these oxidative dye systems is generally paraphenilene-diamine (PPD), for which there is growing evidence of and concern over its carcinogenicity and mutagenicity (The Use of Permanent Hair Dyes and Bladder Cancer Risk, SCCNFP/484/01, 2001). Other oxidative dye system precursors, such as the coupler resorcinol, also show toxicity (David Steiman & Samuel Epstein, The Safe Shopper's Bible, Macmillan, 1995, pp. 240-243). The oxidative action of these types of dye systems is provided by hydrogen peroxide at a high pH, which is known to damage hair and irritate the scalp and skin. Most patented developments in the permanent dye area are aimed at decreasing toxicity, hair damage and irritation (J. F. Corbett, Hair Coloring, Clinics in Dermatology, vol. 6, no. 3, 1988, pp. 96-101).

Semi-permanent hair color formulations are those based on the use of coal tar dyes. Coal tar dyes fall into direct, acid, and basic color index categories. The wash fastness of these dyes is about 2-10 shampoo cycles (Charles Zviak, The Science of Hair Care, Marcel Dekker Inc., New York, 1986, pp. 242-261). Recent studies in toxicology and ecology have identified most coal tar dyes, especially direct (as defined by color index) and mono-azo/di-azo (as defined by structure) dyes (the most red and red-orange shades), as carcinogens, teratogens and mutagens (David Steinman & Samuel Epstein, The Safe Shopper's Bible, Macmillan, 1995, pp. 240-243). Acid dyes in particular are known to stain the scalp and skin. Most patented technologies in this area are aimed at decreasing toxicity and irritation, as well as regulating fastness and leveling. Leveling refers to the process of spreading the color from the dye evenly over the hair.

The toxicity of current permanent and semi-permanent synthetic hair color formulations is such that many U.S. physicians do not recommend hair coloring during pregnancy, for people with cancer, or for people at high risk of cancer (David Steinman & Samuel Epstein, The Safe Shopper's Bible, Macmillan, 1995, p. 241).

The main problems with using natural dyes (as opposed to synthetic hair color formulations) to color hair have always been that natural hair dyes produce dull shades of color and have poor wash fastness to shampoo. Natural sources of dyes, such as plants, contain low concentrations of colorants, and the dyes that are recovered from those natural sources are often impure and have poor solubility (H. S. Freeman & A. T. Peters, Colorants for Non-Textile Applications, Elsevier, 2000, pp. 382-453). These problems result in products with long and inconvenient application times for natural hair color technology. Moreover, most natural hair dyes are offered in powder form, which is inconvenient for the user.

There are a number of different natural plant dyes available. Those plant dyes include, but are not limited to, indigo, indigo carmine, alizarine, rubiethyric acid, purpuroxanthin, rubiadin, morindanigrin, munjistin, morindadiol, carotene, crocetin, bixin, canthaxanthin, lycopene, capsanthin, apocarotenal, xanthophyll, curcumin, morin, malclurin, luteolin, apigenin, fukugetin, datiscetin, kaempferol, rhamnocitrin, rhamnethin, zanthorhamnin, Isorhamnetin, Rhamnazin, Quercetin, Rutin, Gossypetin, Butin/Butein, Rottlerin, Chlorophyll A/B, Catechin, Fisetin, Lapachol, Juglone, Alkannin, Alkannan, Deoxysantalin, Atromentin, Awobamin, Carajuirin, Dracorhodin, Berberine, Betanin, Orcein, Xanthone, Naphthalene, Riboflavin, Anthocyanin, Lawsone, emblica extract, alfalfa extract, black tea extract, green tea extract, white tea extract, and red sandalwood. At present, henna (*Lawsonia intermis*) is the most commonly used natural plant dye for hair. However, due to the poor solubility and low concentration of Lawsone, the pigment in henna, a long application time (as much as several hours) is required to produce a weak, dull shade of color. Moreover, Lawsone "has been examined by SCCNFP . . . (and) . . . its latest opinion on Lawsone . . . (is) Lawsone has genotoxicity/mutagenicity potential in vitro and in vivo and that therefore no safe threshold for Lawsone can be established" (SCCNFP/0798/04, 2004).

Furthermore, natural plant dyes generally lack the color fastness and light fastness of synthetic hair color formulations. Problems with the substantivity of plant-based dyes, which is the affinity that a dye has for a particular fiber, have existed for centuries. Mordanting has long been used as a way to increase substantivity of plant dyes. The mordant's function is to form a complex between a polyvalent metal salt and a dye. The application of a mordant traditionally requires at least two steps, and often includes a pre- or post treatment as well. That is because the reaction between mordants and dyes is virtually instantaneous, making it necessary to apply them separately.

The use of mordants has been limited in recent years, however, because of their generally high toxicity. The most common mordants still in use, although rarely, are chromium salts used in the leather industry. Other mordants include salts of aluminum and copper (Joseph Rivlin, The Dyeing of Textile Fibers, PCT&S, Philadelphia, 1992, p. 30-52; H. S. Freeman & A. T. Peters, Colorants for Non-Textile Applications, Elsevier, 2000, pp. 439-448). There are, however, a number of mineral or metal salts that are capable of acting as a mordant, yet lack the toxicity of chromium salts or other typical mordants. Those mineral or metal salts include, but are not limited to, ferrous gluconate, ferrous aspartate, calcium chloride, calcium gluconate, calcium aspartate, magnesium guconate, magnesium aspartate, magnesium citrate, magnesium palmitate, zinc gluconate, zinc aspartate, and manganese gluconate.

There remains a need for a fast-acting, light fast, wash fast, color fast, natural hair dye formulation which avoids the use of potentially harmful ingredients, and in particular provides bright, intense colors without the use of toxic mordanting agents.

SUMMARY OF THE INVENTION

The present invention addresses the above-described need by providing a composition for dyeing keratin fibers, comprising approximately 0.1 to 30 percent of at least one substantially pure plant dye obtained using at least one of a solvent or supercritical CO2 extraction process, and approximately 0.01 to 5 percent of active metal in a mineral or metallic salt capable of acting as a mordanting agent. The plant dye can be selected from the group consisting of indigo, indigo carmine, alizarine, rubiethyric acid, purpuroxanthin, rubiadin, morindanigrin, munjistin, morindadiol, carotene, crocetin, bixin, canthaxanthin, lycopene, capsanthin, apocarotenal, xanthophyll, curcumin, morin, malclurin, luteolin, apigenin, fukugetin, datiscetin, kaempferol, rhamnocitrin, rhamnethin, zanthorhamnin, Isorhamnetin, Rhamnazin, Quercetin, Rutin, Gossypetin, Butin/Butein, Rottlerin, Chlorophyll A/B, Catechin, Fisetin, Lapachol, Juglone, Alkannin, Alkannan, Deoxysantalin, Atromentin, Awobamin, Carajuirin, Dracorhodin, Berberine, Betanin, Orcein, Xanthone, Naphthalene, Riboflavin, Anthocyanin, Lawsone, emblica extract, alfalfa extract, black tea extract, green tea extract, white tea extract, and red sandalwood. The mineral or metallic salt capable of acting as a mordanting agent can be selected from the group consisting of ferrous gluconate, ferrous aspartate, calcium chloride, calcium gluconate, calcium aspartate, magnesium guconate, magnesium aspartate, magnesium citrate, magnesium palmitate, zinc gluconate, zinc aspartate, and manganese gluconate. One or both parts of the above described composition may be encapsulated in a water impermeable shell so that the composition may be used as a one-part hair dye system. Solvent extraction can include hydrocarbon extraction, ultrafilration, and ion exchange separation. The invention also includes a method of manufacturing a composition for dying hair using the ingredients described above either in combination as a one-part system or separately as a two-part system.

DETAILED DESCRIPTION

In one embodiment of the invention, substantially pure natural plant dyes were obtained by solvent extraction (e.g., hydrocarbon extraction, ultrafiltration, or ion exchange separation) or supercritical CO2 extraction. These substantially pure dyes produced hue, value and chroma results as bright or brighter than those produced by synthetic dyes when applied to keratin fiber (including human hair). This bright color was produced both with and without the use of mordants.

In another embodiment of the invention, we have produced with substantially pure plant dyes (isolated by solvent or supercritical CO2 extraction) bright colors with light and wash fast properties (stable for more than 40 standard shampoo cycles)—comparable or superior to permanent hair dye formulations—by mixing the substantially pure plant dyes with mineral or metallic salts (e.g., zinc gluconate, zinc aspartate, calcium gluconate, or ferrous gluconate among others) in a two-part or two-step system. These mineral or metallic salts are non-toxic salts that function as mordants when mixed with the substantially pure plant dyes isolated as described above.

In a preferred embodiment of the invention, the two-part system described just above comprises 2-20% (w/w) of a substantially pure natural plant dye or combination of dyes, depending on the color desired, isolated by solvent or supercritical CO2 extraction. The balance of the formulation of the first part of the two-part system are diluents, which can include but are not limited to surfactants, emulsifiers, solvents, fragrances, thickeners, humectants, polymers, plasticizers, conditioners, and preservatives. The first part is an aqueous solution. The second part of the two-part system is a zinc salt with 1.75% (w/w) active metal (active zinc as defined by the Cosmetics, Toiletries and Fragrances Association) with the balance diluents in an aqueous solution. Typically, the second part of the two-part solution is rubbed into the hair and allowed to sit for 1-10 minutes, at which point the first part of the two-part solution is added to the hair, rubbed in, and allowed to sit for approximately 20 minutes. The total time is dependent on the color required. For example, if the color being applied was a shade of brown, the longer the solution is left on the hair the darker the shade of brown that will result.

Another useful and unexpected result was obtained when either the substantially pure plant dye and/or the mineral or metallic salt was encapsulated in a lipid, gelatin, calcium alginate, polymethyl methacrylate urea (PMMU), or other water impermeable shell. The encapsulation of either the plant dye, the mineral or metallic salt, or both allows the dye and salt to be combined together into an aqueous solution that can be used in formulations including but not limited to color gels, color creams, color shampoos, color conditioners, and the like. This compatibility is not possible absent the encapsulation step because of the speed with which the mordant reacts with the dye to form an insoluble complex that precipitates out of solution, and is less effective as a dye due to the insoluble complex of mordant and dye forming outside of the presence of keratin fiber. Moreover, these formulations with an encapsulated part are stable for long periods of time (more than 6 months), yet can be applied as a one-step, quick-action hair color (i.e., a one-part system) to color human hair in 10-20 minutes or less.

In a preferred embodiment of the invention, the one-part system described just above comprises the same components, in the same percentages, as the composition for the two-part system described earlier. However, in the one-part system, the zinc salt is encapsulated in a shell of hydrogenated castor oil and/or crosslinked with coacervated gelatin, calcium alginate, or PMMU. Such a coating can be applied by spray drying, fluid bed drying, or any other method known in the art.

Another useful and unexpected result is that the color produced is leveled without the addition of a leveling agent. It will be appreciated that it is often desirable to promote sustained release of either the mineral supplement, the dye, or both after the core amount of both dye and supplement are released. This may be done by providing a gradient of concentrations of both metal action and dye to conduct kinetics on the process as in regular dying systems based on specially synthesized dyes, using techniques known in the art.

By overcoming the problem of compatibility inherent in combining substantially pure plant dyes and mineral or metal salts (acting as a mordant) through the use of encapsulation, natural plant dyes can be used in a one-part system for applications such as:

1. 100% plant-based permanent hair color.
2. 100% plant-based semi-permanent hair color.
3. 100% plant-based demi-permanent hair color
4. 100% plant-based liquid color gel.
5. 100% plant-based color shampoo
6. 100% plant-based color conditioner.
7. 100% plant-based hair color and fixative all in one 8. 100% plant-based hair color and bleach all in one as a hair pretreatment system
9. Any other hair color formulation implying use of natural plant based dye.

The application of all these formulations is very similar to the application of the convenient hair color systems employing conventional synthetic dyes, but without the potential risks of toxicity, irritation and hair damage inherent in those synthetic dye systems.

Thus, by combining the technologies of substantially pure plant dyes obtained by solvent or supercritical CO2 extraction, and mordanting with mineral or metallic salts in combination with or without encapsulation, we have been able to create safe hair dyes that unexpectedly and surprisingly produce bright and permanent or semi-permanent colors similar to synthetic dyes in 10-20 minutes or less, thereby improving on the safety, durability, quality and application time of existing products on the market.

The natural hair dyes described herein are not limited only to the embodiments described. It is contemplated that such embodiments will include not only those described above but also embodiments comprising any number of other ingredients necessary for hair dye products such as those described. Such ingredients would include anionic surfactants, cationic surfactants, nonionic surfactants and amphoteric surfactants, as well as anionic emulsifiers, cationic emulsifiers, nonionic emulsifiers and amphoteric emulsifiers and any other ingredients necessary to practice the invention including but not limited to solvents, fragrances, thickeners, humectants, polymers, plasticizers, conditioners, and preservatives. Numerous other alternatives, modifications and variations will be apparent to those skilled in the art. Accordingly, the invention is intended to encompass all such other embodiments, alternatives, modifications and variations which fall within the scope and spirit of the invention and the claims.

What is claimed is:

1. A composition for dyeing keratin fibers, comprising approximately 0.1 to 30 percent of at least one concentrated plant dye extracted using at least one of a solvent extraction process and a supercritical CO2 extraction process, and a mineral or metallic salt with approximately 0.01 to 5 percent active metal capable of acting as a mordanting agent, and wherein at least one of the concentrated plant dye and the mineral or metal salt capable of acting as a mordanting agent is encapsulated in a water impermeable shell.

2. The composition as defined in claim 1, wherein the salt capable of acting as a mordanting agent is encapsulated in a water impermeable shell.

3. The composition as defined in claim 1, wherein said composition is a one-part hair dye system.

4. The composition as defined in claim 3, wherein said composition is combined with bleach as a pretreatment to form a hair treatment system.

5. The composition as defined in claim 1, wherein at least one concentrated plant dye is selected from the group consisting of indigo, alizarine, rubiethyric acid, purpuroxanthin, rubiadin, morindanigrin, munjistin, morindadiol, carotene, crocetin, bixin, canthaxanthin, lycopene, capsanthin, apocarotenal, xanthophyll, curcumin, morin, maiclurin, luteolin, apigenin, fukugetin, datiscetin, kaempferol, rhamnocitrin, rhamnethin, zanthorhamnin, Isorhamnetin, Rhamnazin, Quercetin, Rutin, Gossypetin, Butin/Butein, Rottlerin, Chlorophyll A/B, Catechin, Pisetin, Lapachol, Juglone, Alkannin, Alkannan, Deoxysantalin, Atromentin, Awobamin, Carajuirin, Dracorhodin, Berberine, Betanin, Orcein, Xanthone, Naphthalene, Riboflavin, Anthocyanin, Lawsone, emblica extract, alfalfa extract, black tea extract, green tea extract, white tea extract, and red sandalwood.

6. The composition as defined in claim 1, wherein the concentrated plant dye is extracted using a solvent extraction process.

7. The composition as defined in claim 6, wherein the solvent extraction process is selected from the group consisting of hydrocarbon extraction, ultrafiltration, and ion exchange separation.

8. The composition as defined in claim 1, wherein the concentrated plant dye is extracted using a supercritical CO2 extraction process.

9. The composition as defined in claim 6, wherein at least one concentrated plant dye is selected from the group consisting of indigo, alizarine, rubiethyric acid, purpuroxanthin, rubiadin, morindanigrin, munjistin, morindadiol, carotene, crocetin, bixin, canthaxanthin, lycopene, capsanthin, apocarotenal, xanthophyll, curcumin, morin, malciurin, luteolin, apigenin, frikugetin, datiscetin, kaempferol, rhamnocitrin, rhamnethin, zanthorhamnin, Isorhamnetin, Rhamnazin, Quercetin, Rutin, Gossypetin, Butin/Butein, Rottlerin, Chlorophyll A/B, Catechin, Fisetin, Lapachol, Juglone, Alkannin, Alkannan, Deoxysantalin, Atromentin, Awobamin, Carajuirin, Dracorhodin, Berberine, Betanin, Orcein, Xanthone, Naphthalene, Riboflavin, Anthocyanin, Lawsone, emblica extract, alfalfa extract, black tea extract, green tea extract, white tea extract, and red sandalwood.

10. The composition as defined in claim 7, wherein at least one concentrated plant dye is selected from the group consisting of indigo, alizarine, rubiethyric acid, purpuroxanthin, rubiadin, morindanigrin, munjistin, morindadiol, carotene, crocetin, bixin, canthaxanthin, lycopene, capsanthin, apocarotenal, xanthophyll, curcumin, morin, malclurin, luteolin, apigenin, fukugetin, datiscetin, kaempferol, rhamnocitrin, rhamnethin, zanthorhamnin, Isorhamnetin, Rhamnazin, Quercetin, Rutin, Gossypetin, Butin/Butein, Rottlerin, Chlorophyll A/B, Catechin, Fisetin, Lapachol, Juglone, Alkannin, Alkannan, Deoxysantalin, Atromentin, Awobamin, Carajuirin, Dracorhodin, Berberine, Betanin, Orcein, Xanthone, Naphthalene, Riboflavin, Anthocyanin, Lawsone, emblica extract, alfalfa extract, black tea extract, green tea extract, white tea extract, and red sandalwood.

11. The composition as defined in claim 8, wherein at least one concentrated plant dye is selected from the group consisting of indigo, alizarine, rubiethyric acid, purpuroxanthin, rubiadin, morindanigrin, munjistin, morindadiol, carotene, crocetin, bixin, canthaxanthin, lycopene, capsanthin, apocarotenal, xanthophyll, curcumin, morin, malciurin, luteolin, apigenin, fukugetin, dati scetin, kaempferol, rhamnocitrin, rhamnethin, zanthorhamnin, Isorhamnetin, Rhamnazin, Quercetin, Rutin, Gossypetin, Butin/Butein, Rottlerin, Chlorophyll A/B, Catechin, Fisetin, Lapachol, Juglone, Alkannin, Alkannan, Deoxysantalin, Atromentin, Awobamin, Carajuirin, Dracorhodin, Berberine, Betanin, Orcein, Xanthone, Naphthalene, Riboflavin, Anthocyanin, Lawsone, emblica extract, alfalfa extract, black tea extract, green tea extract, white tea extract, and red sandalwood.

12. The composition as defined in claim 1, wherein at least one mineral or metallic salt capable of acting as a mordanting agent is selected from the group consisting of ferrous gluconate, ferrous aspartate, calcium chloride, calcium gluconate, calcium aspartate, magnesium gluconate, magnesium aspartate, magnesium citrate, magnesium palmitate, zinc gluconate, zinc aspartate, copper gluconate and manganese gluconate.

13. The composition as defined in claim 1, further comprising a surfactant selected from the group consisting of anionic surfactants, cationic surfactants, nonionic surfactants and amphoteric surfactants.

14. The composition as defined in claim 1, further comprising an emulsifier selected from the group consisting of anionic emulsifiers, cationic emulsifiers, nonionic emulsifiers and amphoteric emulsifiers.

15. A method of manufacturing a composition for dyeing keratin fibers, comprising the steps of:
   using at least one of a solvent extraction process or a supercritical CO2 extraction process to extract a concentrated plant dye;
   combining said concentrated plant dye with a mineral or metallic salt capable of acting as a mordanting agent; and
   encapsulating at least one of said concentrated plant dye and said mineral or metallic salt capable of acting as a mordanting agent in a water impermeable shell.

16. A method as defined in claim 15, wherein the extraction process is a supercritical CO2 extraction process.

17. A method as defined in claim 15, wherein the extraction process is a solvent extraction process.

18. A method as defined in claim 15, wherein at least one concentrated plant dye is selected from the group consisting of indigo, alizarine, rubiethyric acid, purpuroxanthin, rubiadin, morindanigrin, munjistin, morindadiol, carotene, crocetin, bixin, canthaxanthin, lycopene, capsanthin, apocarotenal, xanthophyll, curcumin, morin, malclurin, luteolin, apigenin, fukugetin, datiscetin, kaempferol, rhamnocitrin, rhamnethin, zanthorhamnin, Isorhamnetin, Rhamnazin, Quercetin, Rutin, Gossypetin, ButinlButein, Rottlerin, Chlorophyll A/B, Catechin, Fisetin, Lapachol, Juglone, Alkannin, Alkannan, Deoxysantalin, Atromentin, Awobamin, Carajuirin, Dracorhodin, Berberine, Betanin, Orcein, Xanthone, Naphthalene, Riboflavin, Anthocyanin, Lawsone, emblica extract, alfalfa extract, black tea extract, green tea extract, white tea extract, and red sandalwood.

19. A method as defined in claim 15, wherein at least one mineral or metallic salt capable of acting as a mordanting agent is selected from the group consisting of ferrous gluconate, ferrous aspartate, calcium chloride, calcium gluconate, calcium aspartate, magnesium gluconate, magnesium aspartate, magnesium citrate, magnesium palmitate, zinc gluconate, zinc aspartate, copper gluconate and manganese gluconate.

* * * * *